United States Patent [19]

Ishii et al.

[11] 4,341,900
[45] Jul. 27, 1982

[54] CATALYTIC PROCESS FOR THE PREPARATION OF UNSATURATED CARBOXYLIC ACID

[75] Inventors: Hiromichi Ishii; Hideo Matsuzawa; Masao Kobayashi; Masato Otani, all of Otake, Japan

[73] Assignee: Mitsubishi Rayon Company, Limited, Tokyo, Japan

[21] Appl. No.: 663,361

[22] Filed: Mar. 3, 1976

[30] Foreign Application Priority Data

Mar. 5, 1975 [JP]  Japan ................................. 50-25800
Mar. 5, 1975 [JP]  Japan ................................. 50-26732

[51] Int. Cl.³ ..................... C07C 51/25; C07C 57/055
[52] U.S. Cl. .................................. 562/532; 252/432; 252/435; 252/437; 562/534; 562/535; 562/536
[58] Field of Search ................... 260/530 N; 252/435, 252/437, 432; 562/534, 535, 532

[56] References Cited

U.S. PATENT DOCUMENTS

| | | | |
|---|---|---|---|
| 3,642,930 | 2/1972 | Grasselli et al. | 260/604 R |
| 3,865,873 | 2/1975 | Oda et al. | 260/530 N |
| 3,875,220 | 4/1975 | White et al. | 260/530 N |
| 3,925,464 | 12/1975 | Oda et al. | 260/530 N |
| 3,976,688 | 8/1976 | Akiyama et al. | 260/530 N |
| 4,042,625 | 8/1977 | Matsuzawa et al. | 260/530 N |
| 4,075,244 | 2/1978 | Akiyama et al. | 260/530 NX |

Primary Examiner—Vivian Garner
Attorney, Agent, or Firm—Oblon, Fisher, Spivak, McClelland & Maier

[57] ABSTRACT

The gas phase catalytic oxidation of an unsaturated aldehyde with molecular oxygen at 240° to 450° C. to give the corresponding unsaturated carboxylic acid is conducted in the presence of a catalyst of the following formula:

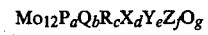

$$Mo_{12}P_aQ_bR_cX_dY_eZ_fO_g$$

wherein Mo is molybdenum, P is phosphorus, O is oxygen, Q is calcium and/or magnesium, R is at least one metal element selected from the group consisting of potassium, rubidium, cesium and thallium, X is at least one element selected from the group consisting of boron, silicon, manganese, iron, cobalt, zinc, germanium, uranium, tin, lead, chromium, titanium, tantalum, antimony, niobium and bismuth, Y is at least one metal element selected from the group consisting of vanadium, copper and nickel, Z is strontium and/or barium, and wherein the subscripts represent the atomic ratio of each component and a is 0.5 to 6, b is 0.2 to 6, c is 0.2 to 6, d is 0.01 to 6, e is 0 to 6, f is 0 to 6, and g is a value determined by the valencies of the elements present in the catalyst.

9 Claims, No Drawings

CATALYTIC PROCESS FOR THE PREPARATION OF UNSATURATED CARBOXYLIC ACID

BACKGROUND OF THE INVENTION

1. Field of the Invention

This invention relates to a process for preparing unsaturated carboxylic acids from unsaturated aldehydes in the presence of a phosphorus-molybdenum-magnesium or calcium type catalyst.

2. Description of the Prior Art

Many processes have been suggested for producing an unsaturated carboxylic acid from an unsaturated aldehyde by a gas-phase oxidazation.

These include, for example, a process for producing acrylic acid from acrolein by using a catalyst consisting of Mo, V, W and silicon (Japanese patent publication No. 12129/1969) and a process for producing acrylic acid by using a catalyst consisting of P, Mo and As (Japanese patent publication No. 19260/1963).

Many processes for producing methacrylic acid have also been suggested. These include the processes of for example, U.S. Pat. No. 3,686,294 (a P-Mo-As catalyst), Japanese patent publication No. 10773/1973 (a catalyst containing Mo and Tl), U.S. Pat. No. 3,795,703 (a P, Mo and alkali metal series catalyst) and Belgian Pat. No. 817100 (a P, Mo and Sb series catalyst). However, from the viewpoint of industrial suitability, these processes are insufficient as regards the selectivity and life time of the catalysts employed.

SUMMARY OF THE INVENTION

Accordingly, an object of the present invention is to provide a novel catalyst for producing acrylic acid or methacrylic acid from acrolein or methacrolein.

Briefly, these and other objects of the present invention as will hereinafter become clear have been attained by providing a process for the preparation of acrylic acid or methacrylic acid by bringing a gaseous mixture containing acrolein or methacrolein and molecular oxygen into contact with a catalyst represented by the following formula in the gas phase at a temperature of 240° to 450° C.;

$$Mo_{12}P_aQ_bR_cX_dY_eZ_fO_g$$

wherein Mo is molybdenum, P is phosphorus, O is oxygen, Q is calcium and/or magnesium, R is at least one metal element selected from among potassium, rubidium, cesium and thallium, X is at least one metal element selected from the group consisting of boron, silicon, manganese, iron, cobalt, zinc, germanium, uranium, tin, lead, chromium, titanium, tantalum, antimony, niobium and bismuth, Y is at least one metal element selected from among vanadium, copper and nickel, Z is strontium and/or barium, subscripts a through g are atomic ratios, wherein a=0.5 to 6, b=0.2 to 6, c=0.2 to 6, d=0.01 to 6, e=0 to 6, f=0 to 6 and g is a value determined by the valencies of the elements present in the catalyst.

DESCRIPTION OF THE PREFERRED EMBODIMENTS

The present process for the production of methacrylic acid from methacrolein results from the discovery of a practical catalyst having a high activity, selectivity, and lifetime which it also has been discovered can be applied to a process for producing acrylic acid from acrolein.

In the catalyst to be used in the present invention, the chemical states of phosphorus, molybdenum and the other metals are so complicated that the chemical state of each component element has not been completely elucidated. It seems probable that each component does not exist as a single oxide but rather is intimately bonded with the others.

It is well known that a catalyst system containing phosphorus and molybdenum is effective for the gas-phase oxidization of acrolein or methacrolein. However, phosphorus and molybdenum produce a very complicated compound whose nature depends on the amounts of each used, the heat-treating temperature and the atmosphere.

Therefore, when a catalyst system containing phosphorus and molybdenum is used for a gas-phase oxidization, the activity and selectivity will often be reduced by variations of the catalyst structure which occur with the passage of time in an ordinarily used reaction temperature range.

However in the catalyst of the present invention, the metals other than phosphorus and molybdenum form very stable salts with phosphorus and molybdenum. This fact seems to contribute to the maintenance of the activity and selectivity.

Among the metals represented by Q in the catalyst of the present invention, magnesium is particularly preferred in respect of the selectivity to methacrylic acid which is produced. Furthermore, when magnesium is used for component Q, cesium is particularly preferred as the R metal.

The metals represented by X are divided into two groups: one displaying excellent effects when coexisting with the metals (such as vanadium, copper and/or nickel) represented by Y and the other displaying excellent effects irrespective of the presence or absence of Y. The former group consists of boron, silicon, manganese, iron, cobalt, zinc, germanium, uranium, tin, lead, chromium and titanium. Among these, iron, boron, cobalt and chromium show particularly desirable effects. Usually from one to four of these metals are used, but it is also possible to use more than four while not significantly impairing the performances of the catalyst.

The metals belonging to the second group are tantalum, antimony, niobium and bismuth. It is also possible to simultaneously use a plurality of these.

The component represented by Y in the catalyst of the present invention is effective to stabilize phosphorus molybdate. It is preferred that when Mo is 12 in terms of atomic ratio, the atomic ratio of the metal Y is 0.01 to 6. Moreover, Z (strontium and/or barium) preferably is present with an atomic ratio of from 0.2 to 6. Particularly, when Q is magnesium, the effect will be most excellent.

Various methods can be used for producing the catalyst of this invention. For example, suitable methods include the conventional evaporation-to-dryness, precipitation and oxide-mixing methods. It is desired that the starting materials be intimately mixed with one another. By way of example, a mixture can be obtained by a method wherein potassium nitrate is added to an aqueous solution of ammonium molybdate and phosphoric acid; then an aqueous solution of calcium nitrate is added and further a powder of tantalum oxide is added, and the mixture is evaporated, dried and solidified. Alternatively, powders of molybdic acid, potassium phosphate, magnesium oxide and antimony oxide can be mixed, or phosphoric acid, an aqueous solution of cesium nitrate and an aqueous solution of magnesium nitrate can be added to an aqueous solution of phosphorus molybdic acid and further niobium oxide and a powder of tantalum oxide can be added, and either mixture then evaporated, dried and solidified. It can then be molded and thereafter heat-treated or first heat-treated and then molded to obtain a catalyst.

Also, the catalyst components may be used on carriers or diluted with such known inert carriers as silica, alumina, silica-alumina and silicon carbide.

Various compounds can be used as starting materials for the catalysts. For example, molybdenum trioxide, molybdic acid, ammonium molybdate and phosphorus molybdic acid can be used for molybdenum.

Phosphoric acid, phosphorus pentoxide, phosphorus molybdic acid and a phosphate can be used for phosphorus.

A nitrate, chloride, phosphate, oxide, carbonate and ammonium salt can be used for the other added metals. Additionally other starting materials can be used which will become oxides when pyrolized, hydrolyzed or oxidized.

The catalyst can be obtained by drying a mixture of the starting materials and then heat treating the mixture at a temperature of 300° to 650° C., especially 350° to 600° C.

The heat-treating time varies depending on the temperature but is usually from 1 hour to scores of hours.

The unsaturated aldehyde to be reacted may contain a small amount of impurities which have no influence on the reaction. These include water or lower saturated aldehydes.

The process of this invention is especially effective for the oxidation of methacrolein. Methacrolein which is obtained by the catalytic oxidation of isobutylene or tertiary butanol can be used as is or after it has been purified.

The concentration of the unsaturated aldehyde in the feed gas can be varied within a broad range, but is preferably 1 to 20% by volume, especially 3 to 10% by volume.

It is economical to use air as the oxygen source but air enriched with pure oxygen can be used if necessary.

The concentration of oxygen in the feed gas is defined by its mole ratio relative to the unsaturated aldehyde. This mole ratio may be 0.3 to 4, especially 0.4 to 2.5.

The starting gaseous mixture may be diluted with inert gases such as nitrogen, steam, carbon dioxide or the like.

The oxidation reaction is conducted under a pressure which may range from the normal pressure to several atmospheres.

The space velocity of the feed gas varies depending on the reaction temperature and pressure, but is generally preferred to be from 300 hr$^{-1}$ to 10,000 hr$^{-1}$.

The reaction temperature can be selected from the range of 240° to 450° C. but is particularly preferred to be 260° to 400° C.

Having generally described this invention, a further understanding can be obtained by reference to certain specific examples which are provided herein for purposes of illustration only and are not intended to be limiting unless otherwise specified.

In the Examples, the term "parts" refers to parts by weight.

The selectivity to the unsaturated carboxylic acid represents the ratio (%) of the molar amount of the unsaturated carboxylic acid product to the molar amount of the reacted unsaturated aldehyde.

The reaction time was measured from the point at which the reaction conditions described in the Examples were actually established.

EXAMPLE 1

42.4 parts of ammonium paramolybdate were dissolved in 200 parts of pure water at about 60° C., 4.04 parts of potassium nitrate and 4.6 parts of 85% phosphoric acid were added thereto. Further, a solution prepared by dissolving 5.13 parts of magnesium nitrate in 50 parts of pure water was added and lastly 4.42 parts of tantalum pentoxide were added. The resulting mixed solution was evaporated to dryness by heating with agitation. The thus obtained cake was dried at 130° C. for 16 hours, was then compression-molded, was sieved to be of 10 to 20 meshes per inch and was calcined at 450° C. for 2 hours to be a catalyst.

The composition of the phosphorus and metal components was of $Mo_{12}$, $P_2$, $Mg_1$, $K_2$, $Ta_1$ in the atomic ratio.

This catalyst was packed in a fixed bed reactor and a gaseous mixture of 5% by volume methacrolein, 10% by volume oxygen, 30% by volume steam and 55% by volume nitrogen was fed into the reactor at a reaction temperature of 340° C. for a contact time of 3.6 seconds. The reaction gas discharged from the reactor was analyzed by gas chromatography. The conversion of the methacrolein was 80.0% and the selectivity to the methacrylic acid was 80.1%. Further, acetic acid, carbon dioxide and carbon monoxide were produced. When the reaction was continued under the same conditions for about 1,000 hours, the conversion of the methacrolein was 79.8% and the selectivity to the methacrylic acid was 80.3%.

EXAMPLES 2 to 11

The following catalysts were prepared in the same manner as in Example 1 and were made to react under the same conditions to obtain the results in Table 1.

TABLE 1

| Example No. | Catalyst Composition (atomic ratio) | reaction time (hr) | reaction temperature (°C.) | conversion of methacrolein (%) | selectivity to methacrylic acid (%) |
|---|---|---|---|---|---|
| 2 | $Mo_{12}P_2Mg_1Rb_2Ta_1$ | 4 | 340 | 80.5 | 80.4 |
|  |  | 1000 | 340 | 80.0 | 80.9 |
| 3 | $Mo_{12}P_2Mg_1Cs_2Ta_1$ | 4 | 340 | 83.5 | 85.3 |
|  |  | 1000 | 340 | 83.2 | 85.9 |
| 4 | $Mo_{12}P_2Mg_1Tl_2Ta_1$ | 4 | 335 | 81.5 | 83.4 |
|  |  | 1000 | 335 | 81.3 | 83.1 |
| 5 | $Mo_{12}P_1Ca_1Cs_2Sb_1$ | 4 | 330 | 82.2 | 85.4 |
| 6 | $Mo_{12}P_1Mg_{0.5}Ca_{0.5}K_1Tl_1Sb_1$ | 4 | 340 | 80.8 | 83.5 |
| 7 | $Mo_{12}P_2Mg_1K_1Cs_1Nb_1$ | 4 | 330 | 82.0 | 85.1 |
|  |  | 1000 | 330 | 81.8 | 85.3 |
| 8 | $Mo_{12}P_2Mg_1K_1Tl_1Bi_1$ | 4 | 330 | 81.8 | 83.4 |
|  |  | 1000 | 330 | 81.7 | 83.0 |
| 9 | $Mo_{12}P_2Mg_1Cs_1Tl_1Ta_{0.5}Nb_{0.5}$ | 4 | 325 | 83.4 | 85.2 |
|  |  | 1000 | 325 | 83.2 | 85.3 |
| 10 | $Mo_{12}P_2Ca_1Cs_2Ta_{0.3}Sb_{0.3}Nb_{0.3}$ | 4 | 320 | 83.6 | 85.8 |
| 11 | $Mo_{12}P_2Mg_1K_1Sb_{0.3}Bi_{0.3}Nb_{0.3}Ta_{0.3}$ | 4 | 315 | 84.0 | 85.9 |

EXAMPLES 12 to 14

The catalysts of Examples 1, 7 and 8 were used for the oxidation of acrolein. The starting gaseous mixture comprised 5% by volume acrolein, 10% by volume oxygen, 30% by volume steam and 55% by volume nitrogen. The reaction temperature and time are shown in Table 2. Contact time was 3.6 seconds. The results are shown in Table 2.

TABLE 2

| Example No. | Catalyst composition (atomic ratio) | reaction time (hr) | reaction temperature (°C.) | conversion of acrolein (%) | selectivity to acrylic acid (%) |
|---|---|---|---|---|---|
| 12 | $Mo_{12}P_2Mg_1K_2Ta_1$ | 4 | 350 | 89.8 | 88.4 |
|  |  | 1000 | 350 | 89.8 | 88.7 |
| 13 | $Mo_{12}P_2Mg_1K_1Cs_1Nb_1$ | 4 | 355 | 93.4 | 93.8 |
| 14 | $Mo_{12}P_2Mg_1K_1Tl_1Bi_1$ | 4 | 350 | 90.5 | 90.4 |

Controls 1 to 3

In the process in Example 1, catalysts of the compositions shown in the following table were respectively prepared and were used for the oxidation of methacrolein under the same conditions as in Example 1 except the reaction temperature to obtain the results in Table 3.

TABLE 3

| Control No. | Catalyst composition (atomic ratio) | reaction time (hr) | reaction temperature (°C.) | conversion of methacrolein (%) | selectivity to methacrylic acid (%) |
|---|---|---|---|---|---|
| 1 | $Mo_{12}P_2Mg_1Ta_1$ | 4 | 390 | 55.9 | 65.4 |
| 2 | $Mo_{12}P_1K_2Sb_1$ | 4 | 390 | 57.4 | 61.4 |
| 3 | $Mo_{12}P_1K_2$ | 4 | 390 | 50.1 | 64.1 |

EXAMPLE 15

42.4 parts of ammonium paramolybdate were dissolved in 200 parts of pure water at about 60° C. 0.70 part of ammonium metavanadate was added thereto to be dissolved. 4.6 parts of 85% phosphoric acid were added thereto, then a solution prepared by dissolving 4.04 parts of potassium nitrate and 5.13 parts of magnesium nitrate in 50 parts of pure water was added, lastly a solution prepared by dissolving 4.04 parts of ferric nitrate in 30 parts of pure water was added and the mixed solution was evaporated to dryness by heating with agitation. The obtained cake was dried at 130° C. for 16 hours, was compression-molded, was crushed to be of 10 to 20 meshes per inch, was sieved and was calcined at 450° C. for 2 hours in an electric furnace.

The catalyst composition so obtained was of $Mo_{12}P_2Mg_1K_2V_{0.3}Fe_{0.5}$. This catalyst was packed in a fixed bed reactor and a gaseous mixture of 5% methacrolein, 10% oxygen, 30% steam and 55% nitrogen by volume was passed through it at a reaction temperature of 300° C. for a contact time of 3.6 seconds. The product was analyzed by gas chromatography. The conversion of methacrolein was 84.0% and the selectivity to the methacrylic acid was 82.5%. Further, acetic acid, carbon dioxide and carbon monoxide were produced. When the reaction was continued under the same conditions for about 1000 hours, the conversion of methacrolein was 82.4% and the selectivity to the methacrylic acid was 84.1%.

EXAMPLES 16 to 33

The following catalysts were prepared in the same manner as in Example 1 and were made to react under the same conditions as in Example 1 to obtain the results in Table 4.

TABLE 4

| Example No. | Catalyst composition (atomic ratio) | reaction time (hr) | reaction temperature (°C.) | conversion of methacrolein (%) | selectivity to methacrylic acid (%) |
|---|---|---|---|---|---|
| 16 | $Mo_{12}P_2Ca_1K_2V_{0.3}Fe_{0.5}$ | 4 | 305 | 80.4 | 82.5 |
|  |  | 1000 | 305 | 80.3 | 83.0 |
| 17 | $Mo_{12}P_1Mg_1Rb_2V_{0.3}Fe_{0.3}$ | 4 | 305 | 81.4 | 82.5 |
| 18 | $Mo_{12}P_1Mg_1Cs_2V_{0.3}Fe_{0.3}$ | 4 | 300 | 83.0 | 86.4 |
| 19 | $Mo_{12}P_1Mg_2Tl_2V_1Fe_{0.5}$ | 4 | 310 | 83.4 | 84.1 |
| 20 | $Mo_{12}P_1Mg_{0.5}Ca_{0.5}K_2V_1Fe_{0.5}$ | 4 | 310 | 81.2 | 82.3 |
| 21 | $Mo_{12}P_1Mg_{0.5}Sr_{0.5}K_1Cs_1V_{0.5}Fe_{0.5}$ | 4 | 315 | 82.4 | 85.8 |
| 22 | $Mo_{12}P_1Mg_{0.5}Ba_{0.5}Cs_2V_{0.5}Fe_{0.5}$ | 4 | 310 | 83.5 | 86.5 |
| 23 | $Mo_{12}P_2Mg_1K_2V_{0.5}B_{0.5}$ | 4 | 320 | 81.5 | 82.9 |
| 24 | $Mo_{12}P_2Mg_1K_2V_{0.5}Si_1$ | 4 | 310 | 81.8 | 83.0 |
| 25 | $Mo_{12}P_2Mg_1K_2V_1Mn_1$ | 4 | 310 | 82.4 | 82.5 |
| 26 | $Mo_{12}P_2Mg_1K_2V_1Co_1$ | 4 | 310 | 82.3 | 82.4 |
| 27 | $Mo_{12}P_2Mg_1K_2V_1Zn_1$ | 4 | 315 | 82.0 | 82.4 |
| 28 | $Mo_{12}P_1Mg_2K_1V_1Ge_1$ | 4 | 310 | 82.1 | 83.1 |
| 29 | $Mo_{12}P_1Mg_2K_1V_1U_{0.5}$ | 4 | 315 | 81.4 | 82.5 |
| 30 | $Mo_{12}P_1Mg_2K_1V_1Sn_{0.5}$ | 4 | 310 | 81.5 | 82.0 |
| 31 | $Mo_{12}P_1Mg_2K_1V_1Pb_{0.5}$ | 4 | 315 | 82.5 | 82.4 |
| 32 | $Mo_{12}P_1Mg_2K_1V_1Cr_{0.5}$ | 4 | 310 | 83.0 | 83.4 |
| 33 | $Mo_{12}P_1Mg_2K_1V_1Ti_{0.5}$ | 4 | 315 | 82.0 | 83.5 |

EXAMPLES 34 and 35

The catalysts shown in Table 5 were prepared in the same manner as in Example 15 and were made to react under the same conditions as in Example 15 except the reaction temperature. The results are shown in Table 5.

TABLE 5

| Example No. | Catalyst composition (atomic ratio) | reaction time (hr) | reaction temperature (°C.) | conversion of methacrolein (%) | selectivity to methacrylic acid (%) |
|---|---|---|---|---|---|
| 34 | $Mo_{12}P_2Mg_1K_2Cu_{0.1}Cr_{0.5}$ | 4 | 290 | 82.0 | 82.5 |
| 35 | $Mo_{12}P_2Mg_1K_2Cu_{0.1}Ti_{0.5}$ | 4 | 295 | 81.5 | 82.0 |

EXAMPLES 36 to 49

In the processes in Examples of Table 6, catalysts were prepared in the same manner by using nickel nitrate instead of ammonium metavanadate or by using ammonium metavanadate and copper nitrate and were made to react under the same conditions as in Example 15 except the reaction temperature. The results are shown in Table 6.

TABLE 6

| Example No. | Catalyst composition (atomic ratio) | reaction time (hr) | reaction temperature (°C.) | conversion of methacrolein (%) | selectivity to methacrylic acid (%) |
|---|---|---|---|---|---|
| 36 | $Mo_{12}P_2Mg_1Cs_2Ni_{0.5}B_{0.5}$ | 4 | 315 | 82.4 | 85.8 |
|  |  | 1000 | 315 | 82.3 | 86.0 |
| 37 | $Mo_{12}P_2Mg_1Cs_2Ni_{0.5}$ | 4 | 310 | 82.0 | 85.7 |

TABLE 6-continued

| Example No. | Catalyst composition (atomic ratio) | reaction time (hr) | reaction temperature (°C.) | conversion of methacrolein (%) | selectivity to methacrylic acid (%) |
|---|---|---|---|---|---|
|  | $Mn_{0.5}$ | 1000 | 310 | 81.8 | 85.8 |
| 38 | $Mo_{12}P_2Mg_{0.5}Cs_1Ni_1Co_{0.5}$ | 4 | 315 | 82.5 | 86.1 |
| 39 | $Mo_{12}P_2Ca_2K_1Ni_1Ge_1$ | 4 | 320 | 81.4 | 83.2 |
| 40 | $Mo_{12}P_1Ca_1K_2Ni_2U_1$ | 4 | 310 | 81.8 | 82.8 |
| 41 | $Mo_{12}P_2Ca_1Cs_1Cu_{0.2}V_1Co_1$ | 4 | 295 | 82.0 | 86.2 |
| 42 | $Mo_{12}P_2Mg_2Cs_2Cu_{0.1}V_{0.5}Cr_{0.5}$ | 4 | 280 | 83.1 | 86.5 |
| 43 | $Mo_{12}P_2Mg_1Cs_1Cu_{0.1}V_{0.3}Si_1Cr_{0.5}$ | 4 | 270 | 83.1 | 86.0 |
| 44 | $Mo_{12}P_2Mg_1Cs_2Cu_{0.1}Cr_{0.5}Sn_{0.5}Si_{0.5}$ | 4 | 275 | 84.2 | 87.4 |
| 45 | $Mo_{12}P_2Mg_1Cs_2Cu_{0.3}Cr_{0.5}Fe_{0.3}Sn_{0.3}Ti_{0.3}$ | 4 | 270 | 84.1 | 87.6 |
| 46 | $Mo_{12}P_2Ca_1Cs_1V_{0.3}B_1$ | 4 | 310 | 83.1 | 86.0 |
| 47 | $Mo_{12}P_2Ca_1Cs_2Cu_{0.3}V_{0.3}Cr_{0.3}$ | 4 | 275 | 83.4 | 88.1 |
| 48 | $Mo_{12}P_2Mg_1Cs_2Cr_{0.5}Co_{0.5}Sb_{0.5}$ | 4 | 295 | 84.1 | 86.1 |
| 49 | $Mo_{12}P_2Ca_1Cs_2Cu_{0.3}Cr_{0.3}Fe_{0.3}Sn_{0.3}Sb_{0.3}$ | 4 | 275 | 83.4 | 86.3 |

EXAMPLES 50 and 51

The catalysts of Examples 15 and 36 were made to react with a gaseous mixture of 5% by volume acrolein, 10% by volume oxygen, 30% by volume steam and 55% by volume nitrogen at a temperature which are shown in the following table for a contact time of 3.6 seconds to obtain the results in Table 7.

TABLE 7

| Example No. | Catalyst composition (atomic ratio) | reaction time (hr) | reaction temperature (°C.) | conversion of acrolein (%) | selectivity to acrylic acid (%) |
|---|---|---|---|---|---|
| 50 | $Mo_{12}P_2Mg_1K_2V_{0.3}Fe_{0.5}$ | 4 | 330 | 90.2 | 90.1 |
|  |  | 1000 | 330 | 90.0 | 90.3 |
| 51 | $Mo_{12}P_2Mg_1Cs_2Ni_{0.5}B_{0.5}$ | 4 | 335 | 93.0 | 94.1 |

What is claimed is:

1. A process for the preparation of unsaturated carboxylic acid, which comprises catalytically oxidizing acrolein, methacrolein or mixtures thereof in the gas phase at a temperature of 240° to 450° C. with molecular oxygen to form the corresponding unsaturated carboxylic acid in the presence of a catalyst represented by the following formula:

$$Mo_{12}P_aQ_bR_cX_dY_eZ_fO_g$$

wherein Mo is molybdenum, P is phosphorus, O is oxygen, Q is calcium, magnesium or a mixture thereof, R is at least one element selected from the group consisting of potassium, rubidium, cesium and thallium, X is at least one element selected from the group consisting of boron, silicon, manganese, iron, cobalt, zinc, germanium, uranium, tin, lead, chromium, titanium, tantalum, antimony, niobium and bismuth, Y is at least one element selected from the group consisting of vanadium, copper and nickel, Z is strontium, barium or a mixture thereof, and wherein a, b, c, d, e, f, and g represent the atomic ratio of each component and a is 0.5 to 6, b is 0.2 to 6, c is 0.2 to 6, d is 0.01 to 6, e is 0.01 to 6, f is 0 to 6, and g is a value determined by the valencies of the elements present in the catalyst.

2. The process of claim 1, wherein X is 1 to 4 elements selected from the group consisting of boron, silicon, manganese, iron, cobalt, zinc, germanium, uranium, tin, lead, chromium and titanium.

3. The process of claim 1, wherein X is at least one element selected from the group consisting of iron, boron, cobalt and chromium.

4. The process of claim 1, wherein the metal Q is magnesium.

5. The process of claim 1, wherein the metal R is cesium.

6. The process of claim 1, wherein the unsaturated aldehyde is methacrolein and methacrylic acid is produced.

7. The process of claim 1, wherein the atomic ratio f is 0.2 to 6.

8. The process of claim 1, wherein f is 0.2 to 6 and cesium is present as one of the metals R.

9. The process of claim 1, wherein the unsaturated aldehyde is acrolein and acrylic acid is produced.

* * * * *

UNITED STATES PATENT AND TRADEMARK OFFICE
CERTIFICATE OF CORRECTION

PATENT NO. : 4,341,900

DATED : July 27, 1982

INVENTOR(S) : Hiromichi Ishii, et al.

It is certified that error appears in the above-identified patent and that said Letters Patent is hereby corrected as shown below:

On the title page, priority data should read

[30] -- Foreign Application Priority Data

March 3, 1975  [JP]  Japan ...50-25800

March 5, 1975  [JP]  Japan....50-26732 --

Signed and Sealed this

Twenty-sixth Day of October 1982

[SEAL]

Attest:

GERALD J. MOSSINGHOFF

Attesting Officer    Commissioner of Patents and Trademarks